(12) United States Patent  
Shibasaki (10) Patent No.: US 8,947,514 B2  
(45) Date of Patent: Feb. 3, 2015

(54) ENDOSCOPE SYSTEM WITH SCANNING FUNCTION

(75) Inventor: Yuichi Shibasaki, Saitama (JP)

(73) Assignee: Hoya Corporation, Tokyo (JP)

(*) Notice: Subject to any disclaimer, the term of this patent is extended or adjusted under 35 U.S.C. 154(b) by 888 days.

(21) Appl. No.: 12/618,886

(22) Filed: Nov. 16, 2009

(65) Prior Publication Data

US 2010/0123775 A1    May 20, 2010

(30) Foreign Application Priority Data

Nov. 14, 2008 (JP) .................. 2008-291846

(51) Int. Cl.
| | |
|---|---|
| A62B 1/04 | (2006.01) |
| H04N 5/225 | (2006.01) |
| A61B 1/00 | (2006.01) |
| A61B 1/04 | (2006.01) |
| A61B 1/06 | (2006.01) |
| A61B 5/00 | (2006.01) |
| G02B 23/24 | (2006.01) |
| G02B 26/10 | (2006.01) |
| H04N 5/235 | (2006.01) |

(52) U.S. Cl.
CPC .......... *H04N 5/2256* (2013.01); *A61B 1/00009* (2013.01); *A61B 1/00172* (2013.01); *A61B 1/043* (2013.01); *A61B 1/0638* (2013.01); *A61B 5/0062* (2013.01); *A61B 5/0084* (2013.01); *G02B 23/2469* (2013.01); *G02B 26/103* (2013.01); *H04N 5/2354* (2013.01); *A61B 1/063* (2013.01); *H04N 2005/2255* (2013.01)
USPC .......................................................... 348/65

(58) Field of Classification Search
CPC ............................... A61B 1/00661; A61B 1/07
USPC .......................................................... 348/65
See application file for complete search history.

(56) References Cited

U.S. PATENT DOCUMENTS 4,622,584 A * 11/1986 Nagasaki et al. .......... 348/69  
4,625,236 A * 11/1986 Fujimori et al. .......... 348/69

(Continued)

FOREIGN PATENT DOCUMENTS

| JP | 61-255318 | 11/1986 |
|---|---|---|
| JP | 5-60984 | 3/1993 |

(Continued)

OTHER PUBLICATIONS

Japan Office action, dated Feb. 5, 2013 along with an english translation thereof.

*Primary Examiner* — Ario Etienne  
*Assistant Examiner* — Blake Rubin  
(74) *Attorney, Agent, or Firm* — Greenblum & Bernstein, P.L.C.

(57) ABSTRACT

An endoscope system has a light source system configured to emit illumination light on a target area, a scanner configured to periodically scan the illumination light over a target area at predetermined time intervals, and an imager configured to receive the illumination light reflected from the target area and to acquire in succession a sequence of image-pixel signals. Further, the endoscope system has a luminance detector that detects in succession a sequence of luminance data of the object image from the sequence of image-pixel signals; and a brightness adjuster that adjusts the brightness of an observed image on the basis of the sequence of luminance data. Then, the brightness adjuster adjusts an amount of illumination light in accordance with a scanning position of the illumination light.

17 Claims, 8 Drawing Sheets

(56) References Cited

U.S. PATENT DOCUMENTS

| | | | |
|---|---|---|---|
| 4,638,353 A * | 1/1987 | Nagasaki et al. | 348/70 |
| 4,710,807 A * | 12/1987 | Chikama | 348/68 |
| 4,803,550 A * | 2/1989 | Yabe et al. | 348/68 |
| 4,834,071 A * | 5/1989 | Hosoi et al. | 600/180 |
| 4,926,258 A * | 5/1990 | Sasaki et al. | 348/72 |
| 5,436,655 A | 7/1995 | Hiyama et al. | |
| 5,995,136 A * | 11/1999 | Hattori et al. | 348/70 |
| 6,294,775 B1 | 9/2001 | Seibel et al. | |
| 6,464,633 B1 * | 10/2002 | Hosoda et al. | 600/178 |
| 6,563,105 B2 | 5/2003 | Seibel et al. | |
| 6,878,109 B2 * | 4/2005 | Yamaki et al. | 600/180 |
| 6,975,898 B2 | 12/2005 | Seibel | |
| 7,029,437 B2 * | 4/2006 | Kobayashi | 600/180 |
| 7,232,410 B2 * | 6/2007 | Takahashi | 600/180 |
| 7,336,894 B2 * | 2/2008 | Ito | 396/17 |
| 7,530,948 B2 | 5/2009 | Seibel et al. | |
| 7,554,572 B2 * | 6/2009 | Takahashi | 348/65 |
| 7,704,206 B2 * | 4/2010 | Suzuki et al. | 600/178 |
| 2001/0055462 A1 * | 12/2001 | Seibel | 385/147 |
| 2002/0139920 A1 * | 10/2002 | Seibel et al. | 250/208.1 |
| 2002/0196335 A1 * | 12/2002 | Ozawa | 348/70 |
| 2003/0001952 A1 * | 1/2003 | Iida et al. | 348/69 |
| 2003/0117491 A1 * | 6/2003 | Avni et al. | 348/77 |
| 2004/0122291 A1 | 6/2004 | Takahashi | |
| 2005/0228231 A1 * | 10/2005 | MacKinnon et al. | 600/180 |
| 2006/0195014 A1 | 8/2006 | Seibel et al. | |
| 2007/0093690 A1 * | 4/2007 | Hopkins et al. | 600/180 |
| 2008/0018734 A1 * | 1/2008 | Iriyama | 348/72 |
| 2008/0039693 A1 * | 2/2008 | Karasawa | 600/175 |
| 2008/0265178 A1 * | 10/2008 | Johnston | 250/492.1 |
| 2009/0105544 A1 * | 4/2009 | Takahira | 600/178 |
| 2009/0135280 A1 * | 5/2009 | Johnston et al. | 348/262 |
| 2009/0141125 A1 * | 6/2009 | Yamazaki | 348/70 |
| 2009/0244260 A1 | 10/2009 | Takahashi et al. | |
| 2009/0244924 A1 | 10/2009 | Enomoto | |

FOREIGN PATENT DOCUMENTS

| | | |
|---|---|---|
| JP | 5-111460 | 5/1993 |
| JP | 10-161041 | 6/1998 |
| JP | 2001-235686 | 8/2001 |
| JP | 2003-135393 | 5/2003 |
| JP | 2003-535659 | 12/2003 |
| JP | 2005-006854 | 1/2005 |
| JP | 2005-6855 | 1/2005 |
| JP | 2005-021423 | 1/2005 |
| JP | 2005-501279 | 1/2005 |
| JP | 2008-531193 | 8/2008 |

* cited by examiner

ENDOSCOPE SYSTEM WITH SCANNING FUNCTION

BACKGROUND OF THE INVENTION

1. Field of the Invention

The present invention relates to an endoscope system that scans illumination light over a target to be observed, such as tissue. In particular, it relates to adjusting the brightness of an observed image.

2. Description of the Related Art

An endoscope system with scanning functionality is equipped with a scanning fiber such as a single mode type fiber, which is provided in an endoscope. As described in Seibel et al. (U.S. Pat. No. 6,294,775), the tip portion of the scanning fiber is held by an actuator such as a piezoelectric device, which vibrates the tip portion spirally by modulating and amplifying the fiber's vibration. Consequently, illumination light passing trough the scanning fiber is spirally scanned over an observation area.

Light reflected off the observation area is entered into an image fiber, and is transmitted to a processor via the image fiber. The transmitted light is transformed to image-pixel signals by photosensors, and one frame's worth of image is generated successively. The spiral scanning is periodically carried out on the basis of a predetermined time-interval (frame rate), and one frame's worth of image-pixel signals are read from the photosensors in accordance with the frame rate.

Usually, the amount of illumination light for one frame interval is nearly uniform over an entire observation area. However, if the depth from the scope tip portion to an observation area is not uniform, a part of the object image may become extremely bright and/or dark. For example, when capturing an inner surface of an organ under condition where the scope tip portion faces an axis of the organ, the center portion of the image becomes too dark, whereas the surrounding portion of the image becomes too bright so that a so-called halation occurs in the surrounding portion. On the other hand, when carrying out image processing for correcting the brightness of an observed image, image quality degrades.

SUMMARY OF THE INVENTION

An object of the present invention is to provide an endoscope system that is capable of adjusting the brightness of an observed image without image processing.

An endoscope system according to the present invention has a light source system configured to emit illumination light on a target area, a scanner configured to periodically scan the illumination light over a target area at predetermined time intervals, and an imager configured to receive the illumination light reflected from the target and to acquire in succession a sequence of image-pixel signals.

For example, a light source that emits R, G, and B light as illumination light and a light source driver that controls the intensity of illumination light are provided. R, G, and B light may be emitted simultaneously. As for the scanner, a fiber driver that vibrates the tip portion of a scanning fiber in two dimensions to scan the illumination light may be provided. Reflected light may be detected by photosensors in the scope tip portion.

The endoscope system has a luminance detector that detects in succession a sequence of luminance data of the object image from the sequence of image-pixel signals; and a brightness adjuster that adjusts the brightness of an observed image on the basis of the sequence of luminance data. The sequence of luminance data may be successively detected in each frame interval, and the brightness is adjusted in each frame interval on the basis of the luminance data detected in a previous frame interval.

In the present invention, the brightness adjuster adjusts an amount of illumination light in accordance with a scanning position of the illumination light. Namely, an amount of illumination light in each frame interval can be changed in time-sequence, which is different from the conventional endoscope system with a scanning function. An amount of illumination light may be adjusted by controlling intensity of light, or by opening/closing a stop (diaphragm).

Since an amount of illumination can be changed in each scanning position, the brightness of an observed image is adjusted in each pixel. Namely, a part of the observed image can be corrected without image processing.

The brightness adjustment may be applied in accordance with various purposes other than a noise reduction. For example, the brightness adjuster may adjust the amount of illumination light incident on a scanning position corresponding to an edge portion of an observed image.

Usually, the center portion of the image becomes too dark, whereas the surrounding portion of the imago becomes too bright during observation. Therefore, the brightness adjuster may increase the amount of illumination light incident on a scanning position corresponding to a pixel having a relatively low luminance level, and may decrease the amount of illumination light incident on a scanning position corresponding to a pixel having a relatively high luminance level. Specifically, the brightness adjuster may adjust the amount of illumination light so as to narrow the range of luminance level variance. In this case, the gray scale of an observed image is maintained before and after the brightness correction.

Also, to make a change of the brightness from the central portion to the surrounding portion a gradual change, the brightness adjuster may increase the illumination light by a large amount as a detected luminance level of a scanning position is low within a relative low range of luminance levels, and may decrease the amount of illumination light by a large amount as a detected luminance level of a scanning position is high within a relative high range of luminance levels. For example, the brightness adjuster increases or decreases the amount of illumination light incident on each scanning position in accordance with a difference between a detected luminance level of a scanning position and a predetermined target luminance level.

When the brightness of an observed image is almost proper, the brightness adjustment may not be carried out. For example, the brightness adjuster suspends an adjustment of the amount of illumination light in a subsequent scanning interval when the percentage of luminance data that fall outside of the upper or lower limit tolerance level is more than a threshold value (for example, 10%).

An apparatus for adjusting the brightness of an observed image according to another aspect of the present invention has a luminance detector that detects in succession a sequence of luminance data of the object image on the basis of a sequence of image-pixel signals that are acquired in succession by illumination light reflected from the target area when periodically scanning the illumination light over the target area; a determiner that determines whether or not a brightness adjustment is necessary, on the basis of the sequence of luminance data; and a brightness adjuster that adjusts the brightness of an observed image on the basis of the sequence of luminance data when the brightness adjustment is necessary. The brightness adjuster adjusts an amount of illumination light in accordance with a scanning position or the illumination light.

A computer readable medium that stores a program for adjusting the brightness of an observed image according to another aspect of the present invention has et luminance detection code segment that detects in succession a sequence of luminance data of the object image on the basis of a sequence of image-pixel signals that are acquired in succession by illumination light reflected from the target area when periodically scanning the illumination light over the target area; a determination code segment that determines whether or not a brightness adjustment is necessary, on the basis of the sequence of luminance data; and a brightness adjustment code segment that adjusts the brightness of an observed image on the basis of the sequence of luminance data when the brightness adjustment is necessary. The brightness adjustment code segment adjusts an amount of illumination light in accordance with a scanning position of the illumination light.

A method for adjusting the brightness of an observed image according to another aspect of the present invention includes: a) detecting in succession a sequence of luminance data of the object image on the basis of a sequence of image-pixel signals that are acquired in succession by illumination light reflected from the target area when periodically scanning the illumination light over the target area; b) determining whether or not a brightness adjustment is necessary, on the basis of the sequence of luminance data; and c) adjusting the brightness of an observed image on the basis of the sequence of luminance data when the brightness adjustment is necessary, the adjusting comprising adjusting an amount of illumination light in accordance with a scanning position of the illumination light.

BRIEF DESCRIPTION OF THE DRAWINGS

The present invention will be better understood from the description of the preferred embodiments of the invention set forth below together with the accompanying drawings, in which.

DESCRIPTION OF THE PREFERRED EMBODIMENTS

Hereinafter, the preferred embodiments of the present invention are described with reference to the attached drawings.

Figure 1:
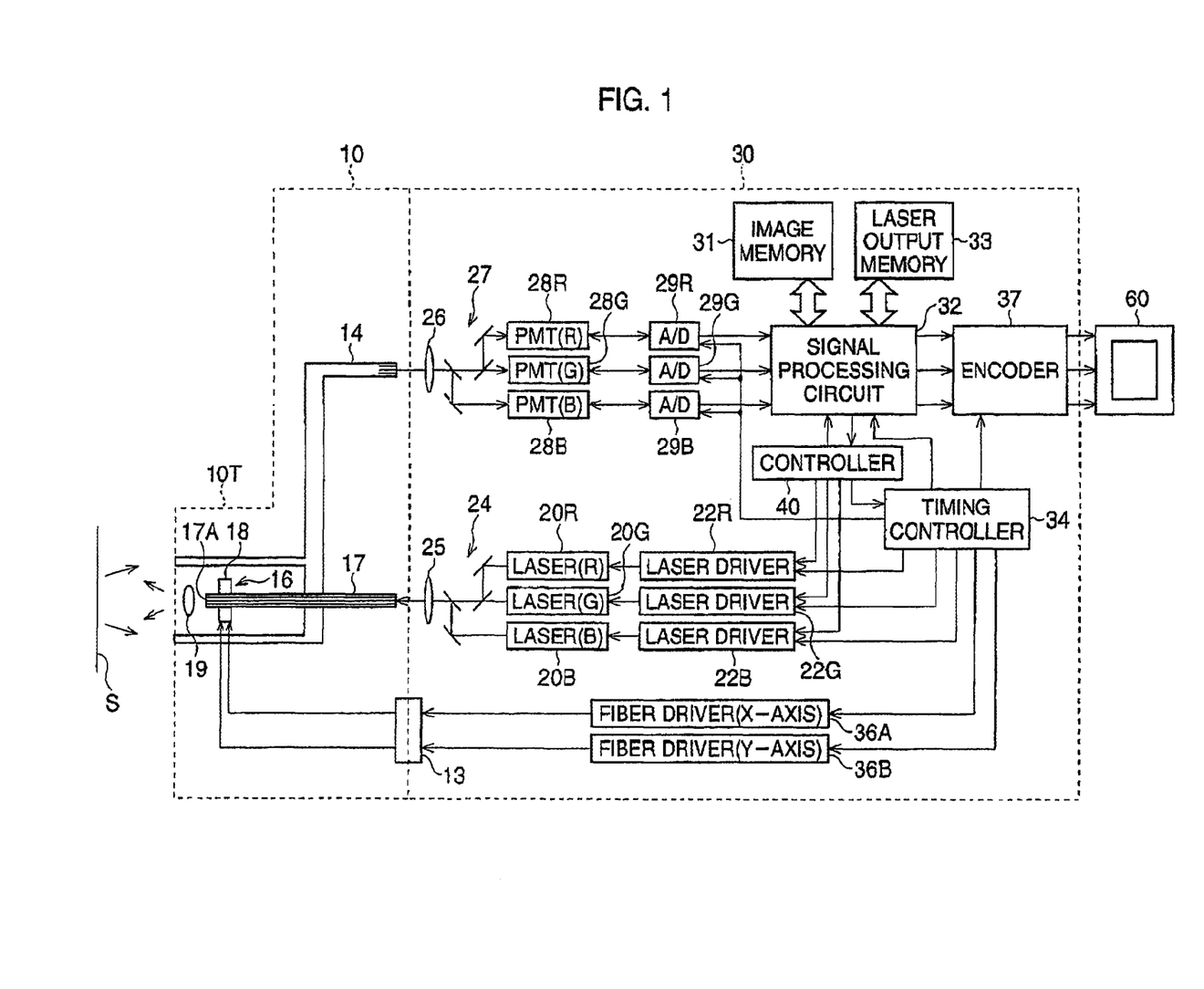
FIG. 1 a block diagram of an endoscope system according to a first embodiment.
Figure 2:
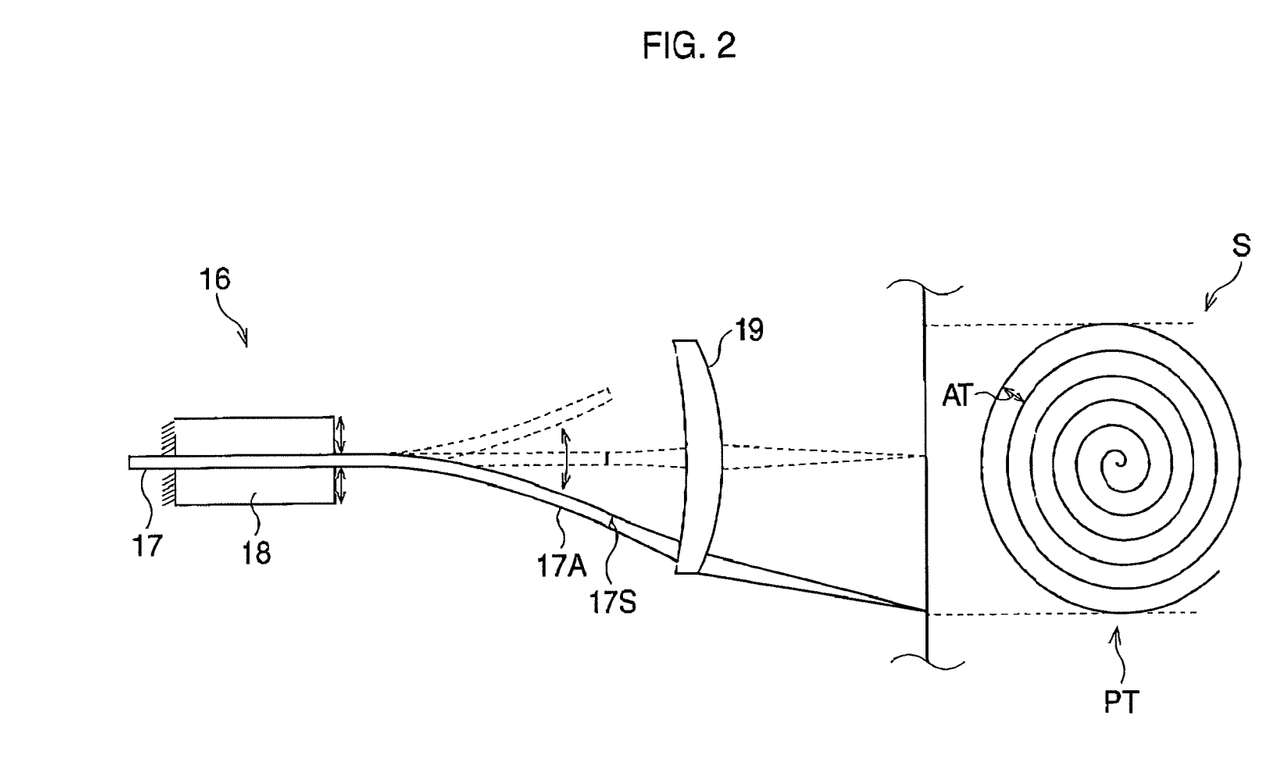
FIG. 2 is an illustration of the scanning optical fiber, scanning unit, and spiral scan pattern.

FIG. 1 is a block diagram of an endoscope system according to a first embodiment. FIG. 2 is an illustration of the scanning optical fiber, scanning unit, and spiral scan pattern.

The endoscope system is equipped with a processor 30 and an endoscope 10 that includes a scanning fiber 17 and an image fiber 14. The single mode type of scanning fiber 17 transmits illumination light, whereas the image fiber 14 transmits light that is reflected off an observation target S such as tissue. The endoscope 10 is detachably connected to the processor 30, and the monitor 60 is connected to the processor 30.

The processor 30 has three lasers 20R, 20G, and 20B, which omit red, green, and blue light, respectively. The lasers 20R, 20G, and 20B are driven by three laser drivers 22R, 22G, and 22B, respectively. The simultaneously emitted red, green, and blue light is collected by half-mirror sets 24 and a collection lens 25. Consequently, white light enters into the scanning fiber 17 and travels to the tip portion 10T of the endoscope 10. The light exiting from the scanning fiber 17 illuminates the target S.

As shown in FIG. 2, a scanning unit 16 is provided in the scope tip portion 10T. The scanning unit 16 has a cylindrical actuator 18 and scans illumination light over the target S. The optical fiber 17 passes through the axis of the actuator 18. The fiber tip portion 17A, which cantilevers from the actuator 18, is supported or held by the actuator 18.

The actuator 10 fixed at the scope tip portion 10T is, herein, a piezoelectric tubular actuator that resonates the fiber tip portion 17A in to dimensions. Concrete speaking, the actuator 18 vibrates the fiber tip portion 17A with respect to two axes that are perpendicular to one other, in accordance with a resonant mode. The vibration of the fiber tip portion 17A spirally displaces the position of the fiber end surface 17S from the axial direction of the optical fiber 17.

The light emitted from the end surface 17S of the scanning fiber 17 passes through an objective lens 19, and reaches the target S. A pattern traced by a scanning beam, i.e., a scan line PT Perms spiral pattern (see FIG. 2). Since a spiral interval AT in a radial direction is tight, the total of the observation area S is illuminated by spirally scanned light.

Light reflected from the target S enters the image fiber 14 and is transmitted to the processor 30. When the reflected light exits from the image fiber 14, it is divided into R, G, and B light by an optical lens 26 and half-mirror sets 27. the separated R, G, and B light then continues on to photosensors 28R, 28G, 28B, respectively, which transforms the R, G, and B light to image-pixel signals corresponding to colors "R", "G" and "B".

The generated analog image-pixel signals are converted to digital image-pixel signals by A/D converters 29R, 29G, and 29B and then fed into a signal processing circuit 32, in which a mapping process is carried out. The successively generated digital R, G, and B image-pixel signals are arrayed in accordance to the order of a spiral scanning pattern. In the mapping process, each of the digital R, G, and B image-pixel signals are associated with a corresponding scanning position, so that raster-arrayed image-pixel signals are formed. Consequently, the pixel position of each of the R, G, and B digital image-pixel signals is identified, in order, and one frame's worth of digital R, G, and B image-pixel signals are generated successively.

In the signal processing circuit 32, the generated two-dimensional image-pixel signals are subjected to various image processing, including a white balance process so that video signals are generated. The generated video signals are sent to the monitor 60 via an encoder 37, thus an observed image is displayed on the monitor 60.

A system controller 40, which includes a ROM unit, a RAM unit, and a CPU, controls the action of the video processor 30 and the videoscope 10 by outputting control signals to the signal processing circuit 32, the laser driver 22R, 22G, and 22B, etc. A control program is stored in the ROM unit. A timing controller 34 outputs synchronizing signals to fiber drivers 36A, 36B for driving the scanning unit 16, the laser driver 22R, 22G, and 22B to synchronize the vibration of the fiber tip portion 17A with the timing of the emission of light. The system controller 40 reads data associated with a brightness adjustment process from an image memory 30 and a laser output memory 33.

The output of lasers 20R, 20G, and 20B is controlled by driving signals fed from the laser drivers 22R, 22G, and 22B, respectively. Thus, an amount of illumination light (intensity of light) incident on a target S is adjustable. In the signal processing circuit 32, luminance signals are generated from the digital image-pixel signals and are transmitted to the system controller 40. The system controller 40 outputs control signals to the laser drivers 22R, 22G, and 22B as to adjust an amount of illumination light in accordance with a scanning position of the illumination light.

Figure 3:
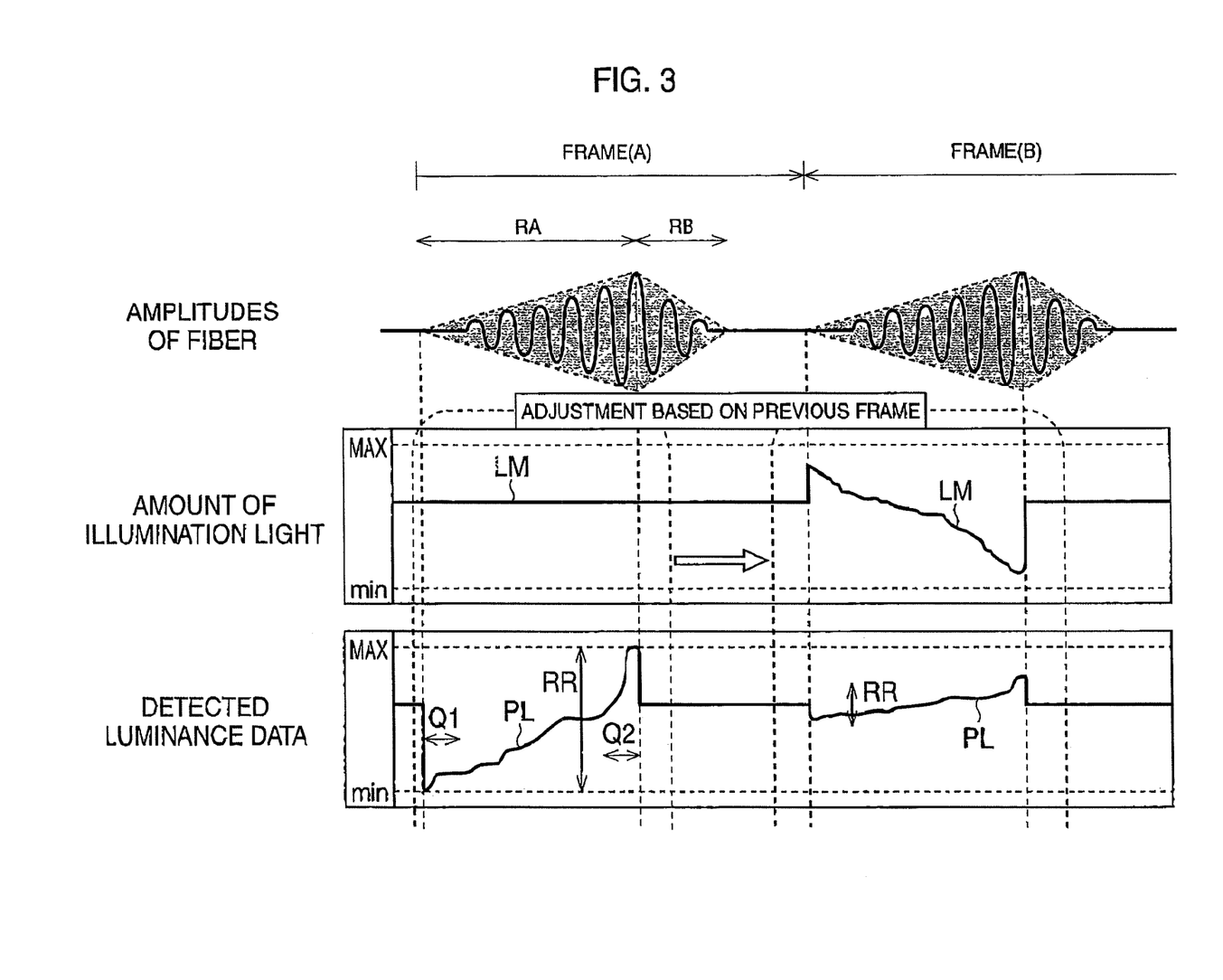
FIG. 3 is a timing chart of a brightness adjustment process.
Figure 4:
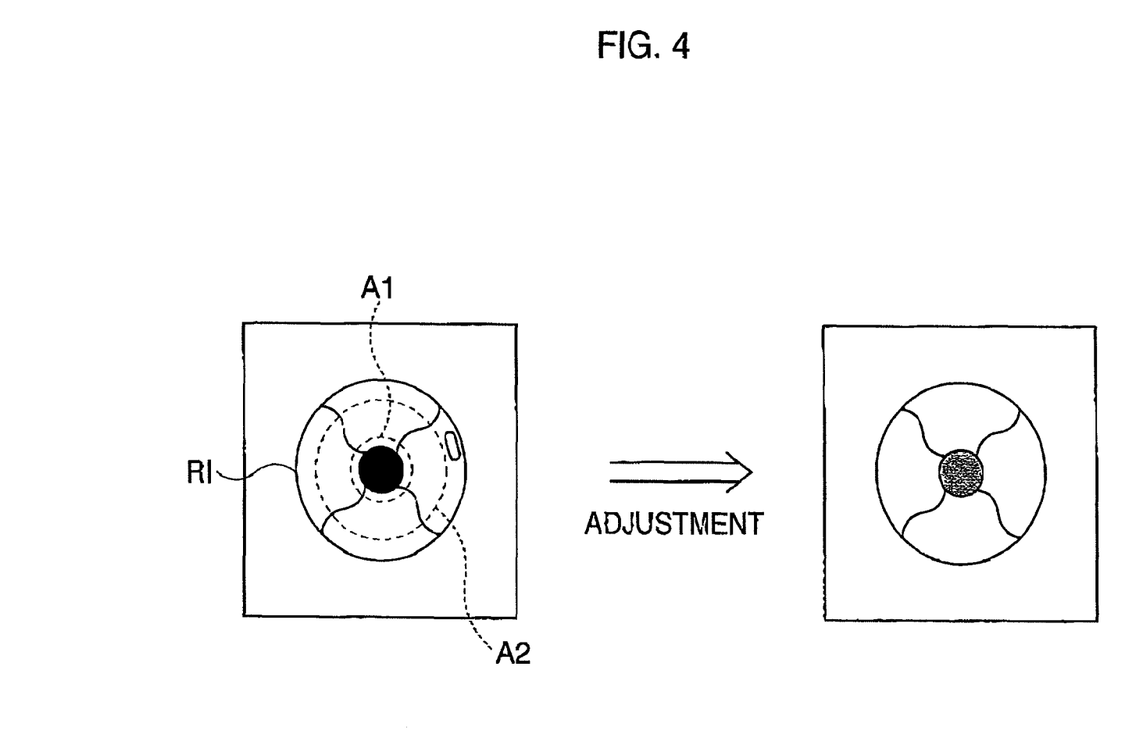
FIG. 4 is an illustration of an observed image displayed on a screen.

FIG. 3 is a timing chart of a brightness adjustment process. FIG. 4 is an illustration of an observed image displayed on a screen. Hereinafter, the adjustment of an amount of illumination light is explained with reference to FIGS. 3 and 4.

In FIG. 3, an amount of illumination light LM emitted from the lasers 20R, 20G, and 20B is shown with the amplitudes of the fiber tip portion 17A, and time-sequence of luminance data PL obtained in time sequence is also shown. One frame's worth of image-pixel signals are detected in an interval "RA", which the fiber tip portion spirally vibrates within one frame interval. The fiber tip portion 17A returns to a central position in an interval "RB" within the same frame interval.

A screen shown in FIG. 4 indicates an observed image when the scope tip portion 10A faces the center of an internal organ such as a digestive organ. The luminance data PL in the frame interval (A) shown in FIG. 3 is obtained based on the image shown in FIG. 4. Note that an amount of illumination light "LM" is herein constant in the frame (A) for ease of explanation. The value of luminance data is, for example, represented in 256 steps (e.g.: a value is in the range of 0 to 255).

In the case of the image shown in FIG. 4, the luminance level of the luminance data PL gradually increases for screen positions that are further away from a central portion A1 and closer to a surrounding portion A2. The center portion A1 of the screen becomes extremely dark, whereas the surrounding portion A2 becomes very bright, so that a so-called halation partially occurs within the surrounding portion A2. Since the scanning line forms a spiral pattern, the luminance level of an interval Q1, corresponding to the central portion A1 of the image, is close to a minimum level in the sequence of the luminance data PL, whereas the luminance level of an interval Q2, corresponding to the image's surrounding portion A2, is close to a maximum level.

Accordingly, while scanning illumination light in a next frame interval, the system controller 40 changes an amount of illumination light in accordance with a scanning position (spot position) in order to adjust the brightness of observed image for each scanned position, i.e., each pixel of the observed image. As shown in FIG. 3, in the next frame interval (B), an amount of illumination light LM is changed in each scanning position, Concretely, the amount of illumination light LM relatively increases at the center portion A1, and relatively decreases at the surrounding portion A2.

Consequently, in frame interval (B), the range RR of luminance levels becomes narrow compared with that of frame interval (A). Thus, a luminance difference between a bright portion and a dark portion of the observed image does not become too large, and the luminance difference is restricted. In FIG. 4, an observed image according to the brightness adjustment in the frame interval (B) is shown. The brightness at both the central portion A1 and the surrounding portion A2 is maintained at a proper brightness. No extreme dark portion or halation exits in the observed image. This brightness adjustment is carried out in each frame interval.

Figure 5:
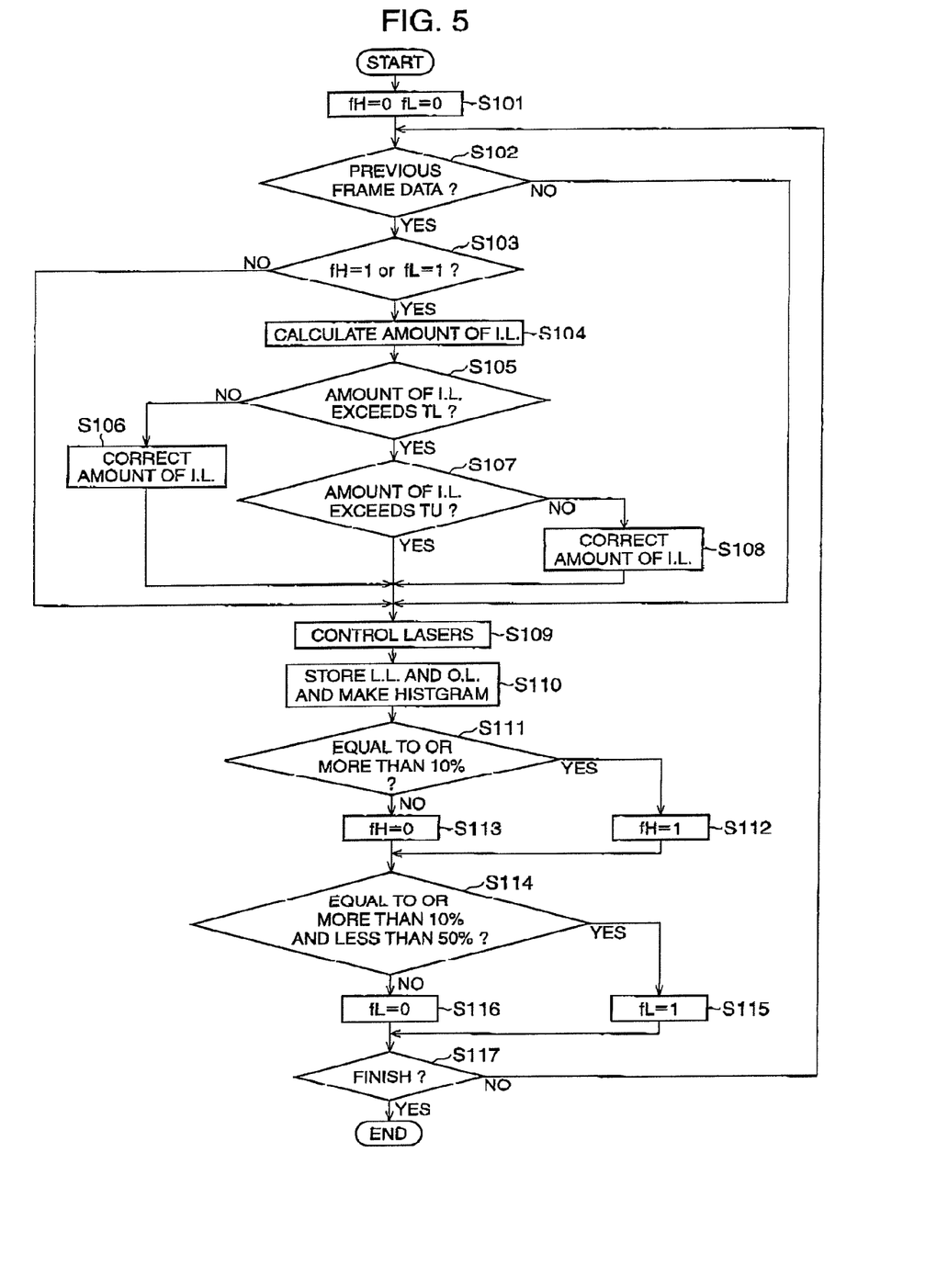
FIG. 5 a flowchart of a brightness adjustment process carried out by the system controller 40.
Figure 6A:
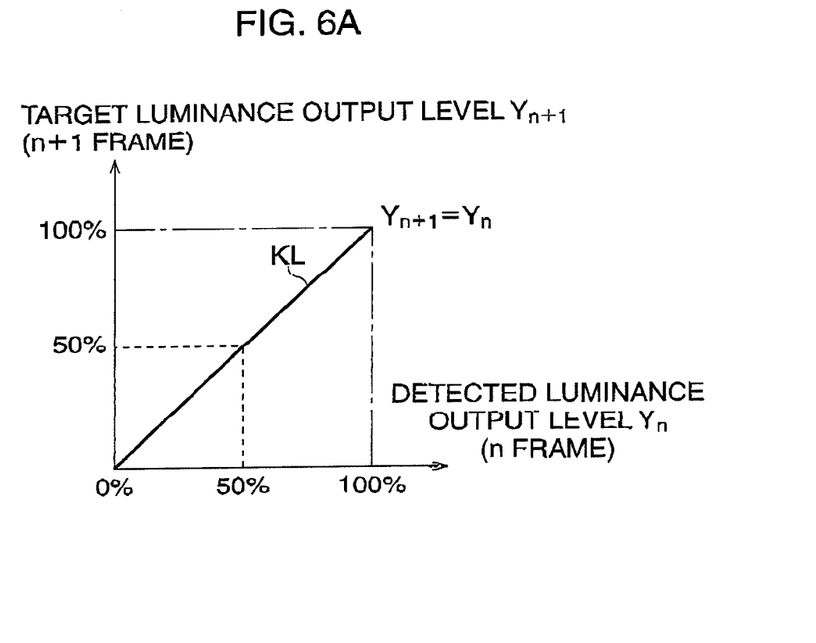
FIGS. 6A and 6B illustrate a relationship between a detected luminance level in a frame interval and a target luminance level in a subsequent frame interval.
Figure 6B:
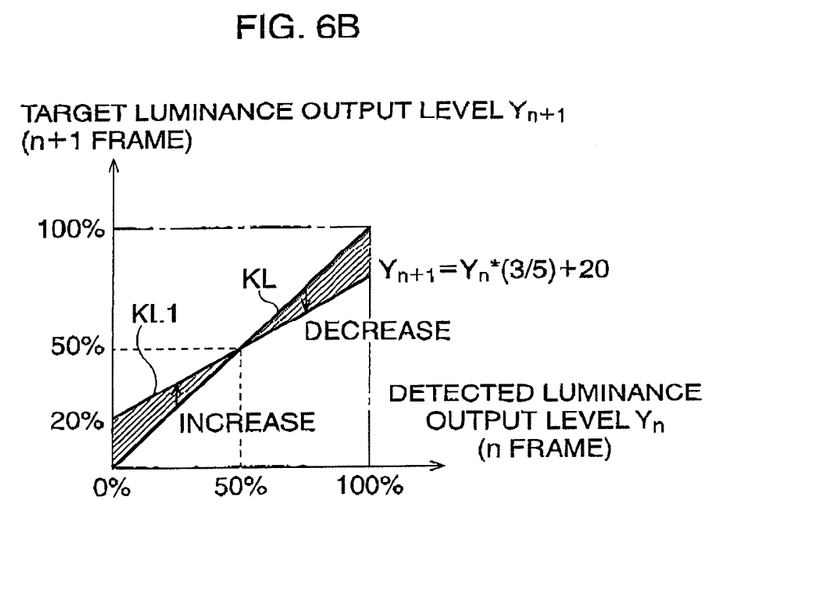
Figure 7:
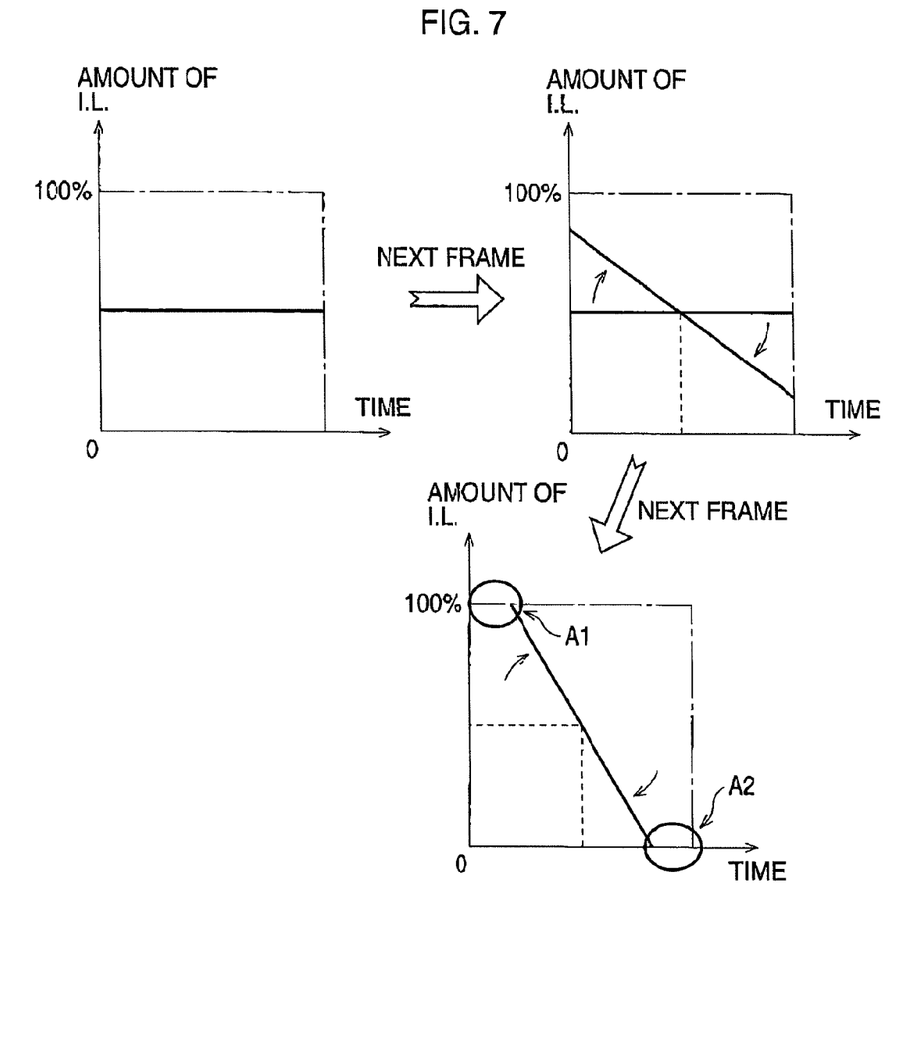
FIG. 7 illustrates a brightness adjustment when an amount of illumination light exceeds a limit value.

FIG. 5 is a flowchart of a brightness adjustment process carried out by the system controller 40. The process is carried out during each scanning cycle (for example, 1/30 time interval). FIGS. 6A and 6B illustrate a relationship between a detected luminance level in a frame interval and a target luminance level in a subsequent frame interval. FIG. 7 illustrates a brightness adjustment when an amount of illumination light exceeds a limit value. The brightness adjustment process is explained with reference to FIGS. 5 to 7.

In Step S101, flags fH and fL are set to zero. The flags fH and fL are variable numbers for determining whether an amount of illumination light should be adjusted in a subsequent frame interval; each flag is set to either 0 or 1. Step 102, a determination is made as to whether or not luminance data and illumination light data from a previous frame interval are stored in the image memory 31 and the laser output memory 33, respectively. When the data in not stored in the image memory 31 and the laser output memory 33, the process proceeds to Step S109.

On the other hand, when it is determined that the data from the previous frame interval are stored in the image memory 31 and the laser output memory 33, the process continues to Step S103, in which it is determined whether the flag fH or the flag fL is 1. as described later, when it is not necessary to adjust an amount of illumination light, the flags fH and fL are set to zero. When it is necessary to adjust an amount of illumination light in a subsequent frame interval, one of the flags fH and fL is set to 1.

In Step S104, an amount of illumination light that is emitted from the lasers 20R, 20G, and 20B is obtained in accordance with the following formulae. Note "$L_{n+1}$" represents an output level in the number "n+1" frame interval, and "$L_n$" represents an output level in the number "n" frame interval.

$$L_{n+1}=L_n-L_n*(Y_n-Y_{n+1})/100 \tag{1}$$

(Note $Y>Y_{max}/2$)

$$L_{n+1}=L_n+L_n*(Y_n-Y_{n+1})/100 \tag{2}$$

(Note $Y_n \leq Y_{max}/2$)

"$Y_n$" indicates a detected luminance level of each scanning position (pixel), which is detected in the number "n" frame interval. On the other hand, "$Y_{n+1}$" indicates a target luminance level of each pixel at the number "n+1" frame interval. As shown in the following formula, "$Y_{n+1}$" is represented as a function of "$Y_n$".

$$Y_{n+1}=Y_n*(3/5)+20 \tag{3}$$

Hereinafter, a brightness correction represented by formulas (1) to (3) is explained in detail. The graph shown in FIG. 6A, illustrates a relationship between "$Y_n$" and "$Y_{n+1}$" in a state that the brightness adjustment is not needed. The vertical axis represents a target luminance level "$Y_{n+1}$" in the number "n+1" frame interval. Note the value of the target luminance level is designated by a percentage (%) of a maximum luminance level. The horizontal axis represents a detected luminance level "$Y_n$" (also a percentage of the maximum) in the number "n" frame interval.

If the brightness adjustment is not carried out in the number "n+1" frame interval, then a target luminance level "$Y_{n+1}$" is directly set to the detected luminance level "$Y_n$". Since a target luminance level "$Y_{n+1}$" in a given pixel coincides with a corresponding detected luminance level "$Y_n$", a relationship between a target luminance level "$Y_{n+1}$" and a detected luminance level "$Y_n$" is represented by a straight line XL.

Therefore, a laser output level "$L_{n+1}$" in the number "n+1" frame interval is directly set to a laser output level from the number "n" frame interval, as can be seen from formulas (1) and (2). The output levels of the lasers 20R, 20G, and 20B are the same as each other.

On the other hand, when carrying out a brightness correction, the luminance level "Yn+1" in the number "n+1" frame interval is decided in accordance with formula (3). In FIG. 6B, a straight line KL1 is shown. The laser output level "Ln+1" is calculated in accordance with formula (1) or (2). Based on the detected luminance level "Yn", it is determined whether an amount of illumination light should be increased or decreased. Concretely, when a detected luminance level "Yn" is greater than 50% of the maximum luminance level "Ymax", the illumination light is decreased by an amount determined by formula (1). When the luminance level "Yn" is equal to or less than 50% of the maximum luminance level "Ymax", the illumination light is increased by an amount determined by formula (2).

The laser output level "$L_{n+1}$" is set such that an amount of illumination light becomes smaller as a detected luminance level "$Y_n$" is higher, and becomes larger as a detected luminance level "$Y_n$" is lower, as shown by the straight line KL1. The decreasing/increasing amount depends upon a difference between "$Y_n$" and "$Y_{n+1}$".

This brightness correction narrows the range of target luminance levels. In FIG. 6B, the range of target luminance levels changes from the range 0-100% to the range 20%-80%. Thus, an extremely dark or halation portion does not occur. The brightness correction is carried out in each scanning position or pixel. After the process in Step S104 is carried out, the process continues to Step S105.

In Step S105, it is determined whether a laser output level calculated by either formula (1) or (2) is greater than or equal to an upper limit value TL. The upper limit value TL is predetermined in accordance to the performance of the lasers 20R, 20G, and 20B. When it is determined that the calculated laser output level is greater than the upper limit value TL, an actual laser output level is set to the upper limit value TL (S106).

In Step S107, it is determined whether a laser output level calculated by either formula (1) or (2) is less than or equal to a lower limit value TU. When it is determined that the calculated laser output level is less than the lower limit value TU, an actual laser output level is set to the lower limit value (S108).

Hereinafter, the processes of Steps S105 to S108 are explained in detail, In FIG. 7, a change in an amount of illumination light is shown. In the first frame interval, the amount of illumination light is constant. Note that the horizontal axis represents a scanning time of one frame interval. In the next frame interval the amount of illumination light is adjusted by a quantity that is determined by either formula (1) or (2), such that the amount of illumination light gradually decreases. Namely, an amount of illumination light increases the closer it is to the center of an observed image, but decreases as it becomes closer to the outer portion.

If further brightness correction is necessary, an amount of illumination light in the next frame interval could increase or decreases the amount of illumination light too much at the center portion A1 or the surrounding portion A2 of the observed image. In this case, the calculated laser output level is either greater than the upper limit value TL or less than the lower limit value TU. Therefore, the calculated laser output level is changed or corrected to the upper limit value TL or lower limit value TU at the center portion A1 or the surrounding portion A2 of the observed image.

After an amount of illumination light is decided for each pixel in Steps 104-108, in Step S109 the output levels of the lasers 20R, 20G, and 20B are controlled in accordance to the decided amount. The amount of illumination light in a subsequent frame interval is adjusted in accordance with the vibration of the fiber tip portion 17A.

In Step S110, laser output levels obtained in Step S104 are stored in the output level memory 33. Also, a luminance level for each spot or pixel is detected during a spiral scanning procedure. The luminance level of one detected frame is stored in the image memory 31. Herein, histogram data of the luminance levels and the laser output levels are generated and stored in the image memory 31 and the output level memory 33, respectively.

In Step S111, it is determined whether a percentage of luminance levels that exceed an upper limit tolerance value WU is equal or greater than 10% of one frame's worth of detected luminance levels. The predetermined upper limit tolerance value WU represents an upper level of the luminance range that does not interfere with an observation. When the percentage is found to be equal or greater than 10%, it is determined that carrying out the brightness correction in the next frame interval is necessary, and the flag fH is set to 1 (Step 112). On the other hand, when the percentage is found to be smaller than 10%, the brightness correction is not carried out in a next frame interval and the flag fH is set to 0 (S113).

In Step S114, it is determined whether the percentage of luminance levels that are below a lower limit tolerance value WL is equal to or greater than 10% of one frame's worth of detected luminance levels, and whether the percentage of calculated laser output levels that exceed the upper limit value TL described in Step S105 is less than 50%. The lower limit tolerance value WL represents a limit level that does not interfere with an observation.

When the percentage of luminance levels that are below a lower limit tolerance value WL is equal to or greater than 10%, and 50% or less of the calculated laser output levels exceed the limited upper value TL, it is determined that carrying out the brightness correction in the next frame interval is necessary, and the flag fL is set to 1 (Step 115). On the other hand, when it is determined that the percentage of luminance levels is less than 10%, or more than 50% of the calculated laser output levels exceed the limited upper value TL, it is determined that the brightness correction in the next frame interval is not carried out and the flag fL is set to 0 (S116).

In Step S117, it is determined whether an operation for terminating an observation has been performed. When it is determined that the operation has been performed, the process is terminated.

In this way, in the present embodiment, the fiber tip portion 17A vibrates spirally in earth frame interval while scanning illumination light over a subject that is observed successively. Thus, one frame's worth of luminance data is detected subsequently. When an extreme dark portion and/or halation portion, which exceeds a tolerance level, exists in an observed image (Steps S111 and S113), the brightness correction is carried out in the next frame interval (Steps S112 and S115).

In the next frame interval, an amount of illumination light, namely laser output levels of the lasers 20R, 20G, and 20B, are calculated on the basis of formulas (1) to (3) (Steps S104, S106, and S108). A decreasing or increasing amount of illumination light is determined on the basis of a difference between a target luminance level and a detected luminance level in each pixel. Then, the lasers 20R, 20G, and 20B are controlled in accordance to a scanning position or pixel such that a laser output level is decreased for a pixel having a relatively high luminance level in the previous frame interval, whereas an a laser output level is increased for a pixel having a relatively low luminance level (Step S109). If the brightness correction is not necessary, a brightness adjustment process is not carried out in a subsequent frame interval (Steps S103, S113, and S116).

The brightness correction based on formulas (1) to (3) maintains a degree of a gray scale in an object image before and after the brightness correction. In addition, the brightness correction makes the change of the brightness from the center portion to the surrounding portion a gradual change. Thus, an operator can diagnose an issue with ease by observing an object image with a proper brightness.

Figure 8:
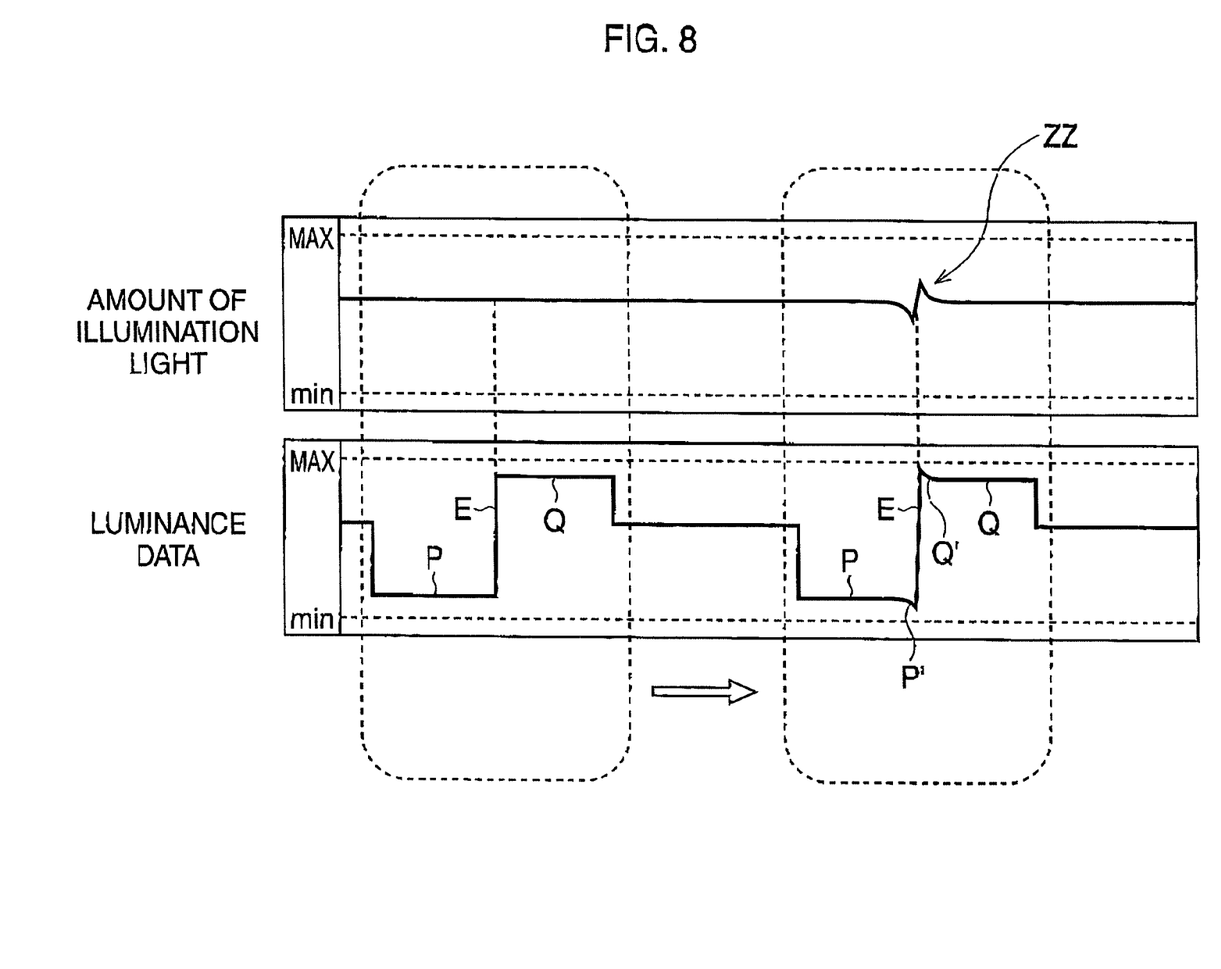
FIG. 8 is a timing chart of a luminance level and an amount of illumination light according to the second embodiment.

With reference to FIG. 8, the second embodiment is explained. The second embodiment is different from the first embodiment in that a brightness adjustment process is carried out to enhance an edge or contoured portion of an observed image.

FIG. 8 is a timing chart of a luminance level and an amount of illumination light according to the second embodiment. Luminance data shown in FIG. 8 include an edge portion E that corresponds to a boundary between a dark portion P and a bright portion Q. The dark portion P exists in a central portion of an observed image, whereas the bright portion Q exists in the surrounding portion. In this case, the laser output levels of the lasers 20R, 20G, and 20B are controlled such that the edge portion E is emphasized in a subsequent frame interval. Concretely, a laser output level is controlled so as to cause a difference to occur substantially before and after an edge portion E as shown in an arrow ZZ. Thus, a difference between a high luminance level P' and a low luminance level Q' adjacent to the edge portion E is enlarged and the contours of an object image are clearly displayed.

In the first and second embodiments, the brightness adjustment process is carried out in each frame interval. However, a luminance detection process and an output adjustment process may be carried out alternately over two frame intervals. In this case, for example, a luminance level is detected in the first frame interval in a state of constant illumination light, and a laser output level is adjusted in the second frame interval.

The brightness correction may be carried out for an optional purpose other than a noise reduction process for eliminating halation, extreme darkness, or an edge enhancement such as described. Furthermore, a laser output level may be calculated by a method other than that shown in formulas (1) to (3). For example, a brightness adjustment process may be carried out for only pixels corresponding to a halation portion.

As for the scanning procedure, a construction other than the scanning fiber may be applied. For example, illumination light may be scanned by driving an optical lens provided in the fiber. Also, a laser output level may be adjusted in each of the R, G, and B light. Furthermore, a light source system other than a laser system may be applied.

The present disclosure relates to subject matter contained in Japanese Patent Application No. 2008-291846 (filed on Nov. 14, 2008), which is expressly incorporated herein, by reference, in its entirety.

The invention claimed is:

1. An endoscope system comprising:
a light source system configured to emit illumination light on a target area;
a scanner configured to periodically scan the illumination light over a target area, said scanner comprising a fiber driver that vibrates a tip portion of a scanning fiber in two dimensions to scan the illumination light, vibration of the tip portion of the scanning fiber determining a scan path of the illumination light, the scan path in each frame occurs over a time interval defining a frame of an object image;
an imager configured to receive the illumination light reflected from the target area and to acquire a sequence of image-pixel signals in succession;
a luminance detector that detects, in succession, a sequence of luminance data of the object image from the sequence of image-pixel signals; and
a brightness adjuster that adjusts the brightness of an observed image on the basis of the sequence of luminance data, said brightness adjuster adjusting an amount of illumination light in accordance with a scanning position of the illumination light on the scan path, such that the amount of illumination light in the frame which occurs over the time interval is time-sequentially changed,
wherein the brightness adjuster determines the amount of illumination light in a current frame by correcting the amount of illumination light in a previous frame.

2. The endoscope system of claim 1, wherein said brightness adjuster increases the amount of illumination light incident on a scanning position corresponding to a pixel having a luminance level less than 50% of a maximum luminance level, and decreases the amount of illumination light incident on a scanning position corresponding to a pixel having a luminance level greater than 50% of the maximum luminance level.

3. The endoscope system of claim 1, wherein said brightness adjuster adjusts the amount of illumination light so as to narrow the range of luminance level variance.

4. The endoscope system of claim 1, wherein said brightness adjuster increases the illumination light by a larger amount as a detected luminance level of a scanning position decreases when the detected luminance level of the scanning position is less than 50% of a maximum luminance level, and decreases the amount of illumination light by a larger amount as a detected luminance level of a scanning position increases when the detected luminance level of the scanning position is greater than 50% of a maximum luminance level.

5. The endoscope system of claim 1, wherein said brightness adjuster increases or decreases the amount of illumination light incident on each scanning position in accordance with a difference between a detected luminance level of a scanning position and a predetermined target luminance level.

6. The endoscope system of claim 1, wherein said brightness adjuster suspends adjustment of the amount of illumination light in a subsequent scanning interval when a percentage of luminance data that fall outside of an upper or lower limit tolerance level is more than a threshold value.

7. The endoscope system of claim 1, wherein said brightness adjuster adjusts the amount of illumination light incident on a scanning position corresponding to an edge portion of an observed image.

8. The endoscope system of claim 1, wherein said light source system comprises:
a light source that emits R, G, and B light as illumination light; and
a light source driver that controls the intensity of illumination light.

9. An apparatus for adjusting the brightness of an observed image according to an endoscope system, comprising:
a luminance detector that detects, in succession, a sequence of luminance data of the object image on the basis of a sequence of image-pixel signals that are acquired in succession by illumination light reflected from the target area, while a scanner periodically scans the illumination light over the target area by vibrating a tip portion of a scanning fiber in two dimensions, vibration of the tip portion of the scanning fiber determining a scan path of the illumination light, the scan path in each frame occurs over a time interval defining a frame of an object image;
    a determiner that determines whether or not a brightness adjustment is necessary, on the basis of the sequence of luminance data; and
    a brightness adjuster that adjusts the brightness of an observed image on the basis of the sequence of luminance data when the brightness adjustment is necessary, said brightness adjuster adjusting an amount of illumination light in accordance with a scanning position of the illumination light on the scan path, such that the amount of illumination light in the frame which occurs over the time interval is time-sequentially changed,
    wherein the brightness adjuster determines the amount of illumination light in a current frame by correcting the amount of illumination light in a previous frame.

10. A non-transitory computer readable medium that stores a program executable by a computer, for adjusting the brightness of an observed image according to an endoscope system, the program comprising:
    a luminance detection code segment that detects, in succession, a sequence of luminance data of the object image on the basis of a sequence of image-pixel signals that are acquired in succession by illumination light reflected from the target area, while a scanner periodically scans the illumination light over the target area by vibrating a tip portion of a scanning fiber in two dimensions, vibration of the tip portion of the scanning fiber determining a scan path of the illumination light, the scan path in each frame occurs over a time interval defining a frame of an object image;
    a determination code segment that determines whether or not a brightness adjustment is necessary, on the basis of the sequence of luminance data; and
    a brightness adjustment code segment that adjusts the brightness of an observed image on the basis of the sequence of luminance data when the brightness adjustment is necessary, the brightness adjustment code segment adjusting an amount of illumination light in accordance with a scanning position of the illumination light on the scan path, such that the amount of illumination light in the frame which occurs over the time interval is time-sequentially changed,
    wherein the brightness adjustment code segment determines the amount of illumination light in a current frame by correcting the amount of illumination light in a previous frame.

11. A method for adjusting the brightness of an observed image according to an endoscope system, comprising:
    detecting, in succession, a sequence of luminance data of the object image on the basis of a sequence of image-pixel signals that are acquired in succession by illumination light reflected from the target area, while a scanner periodically scans the illumination light over the target area by vibrating a tip portion of a scanning fiber in two dimensions, vibration of the tip portion of the scanning fiber determining a scan path of the illumination light, the scan path in each frame occurs over a time interval defining a frame of an object image;
    determining whether or not a brightness adjustment is necessary, on the basis of the sequence of luminance data; and
    adjusting the brightness of an observed image on the basis of the sequence of luminance data when the brightness adjustment is necessary, the adjusting comprising adjusting an amount of illumination light in accordance with a scanning position of the illumination light on the scan path, such that the amount of illumination light in the frame which occurs over the time interval is time-sequentially changed,
    wherein the adjusting determines the amount of illumination light in a current frame by correcting the amount of illumination light in a previous frame.

12. The endoscope system according to claim 1, wherein the fiber driver vibrates the tip portion of the scanning fiber such that the illumination light is scanned spirally.

13. The apparatus according to claim 9, wherein the tip portion of the scanning fiber vibrates such that the illumination light is scanned spirally.

14. The non-transitory computer readable medium according to claim 10, wherein the tip portion of the scanning fiber vibrates such that the illumination light is scanned spirally.

15. The method according to claim 11, wherein the tip portion of the scanning fiber vibrates such that the illumination light is scanned spirally.

16. The endoscope system according to claim 1, wherein the scanner is provided in a tip portion of the endoscope, and the fiber driver vibrates the tip portion of the scanning fiber such that the scanning position of the illumination light changes, while the position of the tip portion of the endoscope does not change.

17. The endoscope system according to claim 1, wherein the brightness adjuster determines the amount of illumination light of a scanning position on the scan path in the current frame by correcting the amount of illumination light on a corresponding scanning position on the scan path in the previous frame.

* * * * *